United States Patent
Morrison, Jr. et al.

(10) Patent No.: US 8,517,595 B2
(45) Date of Patent: Aug. 27, 2013

(54) APPARATUS AND METHOD FOR MIXING BY PRODUCING SHEAR AND/OR CAVITATION, AND COMPONENTS FOR APPARATUS

(75) Inventors: Lowen Robert Morrison, Jr., Cincinnati, OH (US); Ke-Ming Quan, West Chester, OH (US); Raul Victorino Nunes, Loveland, OH (US); Vesselin Nikolov Shanov, Cincinnati, OH (US); Paul Alfred Cimiluca, Cincinnati, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 968 days.

(21) Appl. No.: 12/147,629

(22) Filed: Jun. 27, 2008

(65) Prior Publication Data
US 2009/0003123 A1    Jan. 1, 2009

Related U.S. Application Data

(60) Provisional application No. 60/937,501, filed on Jun. 28, 2007.

(51) Int. Cl.
*B01F 11/00*    (2006.01)
*B01F 15/02*    (2006.01)

(52) U.S. Cl.
USPC .................... 366/119; 366/124; 366/175.2

(58) Field of Classification Search
USPC .................................. 366/119, 124, 175.2
See application file for complete search history.

(56) References Cited

U.S. PATENT DOCUMENTS

| | | | | |
|---|---|---|---|---|
| 2,713,998 A | * | 7/1955 | Eicken | 366/119 |
| RE25,324 E | * | 1/1963 | Cottell et al. | 366/119 |
| 3,176,964 A | * | 4/1965 | Cottell et al. | 366/119 |
| 3,278,165 A | * | 10/1966 | Gaffney | 366/119 |
| 3,285,579 A | * | 11/1966 | Guerin | 366/119 |
| 3,357,683 A | * | 12/1967 | Frykhult | 366/119 |
| 3,399,031 A | | 8/1968 | McCarthy | |
| 3,408,050 A | * | 10/1968 | Jacobs, III | 366/119 |

(Continued)

FOREIGN PATENT DOCUMENTS
WO    WO 99/44413 A1    9/1999

OTHER PUBLICATIONS

K.A. Schwetz, "Wear of boron carbide ceramics by abrasive waterjets", Wear 181-183 (1995) 148-155, Elsevier Science S.A. copyright 1995.*
PCT International Search Report, Mailed Jan. 7, 2009, 6 Pages.

*Primary Examiner* — Tony G Soohoo
(74) *Attorney, Agent, or Firm* — Alexandra S. Anoff (57) ABSTRACT

An apparatus and method for mixing by producing shear and/or cavitation, and components for the apparatus are disclosed. In one embodiment, the apparatus includes a mixing and/or cavitation chamber with an element such as an orifice component that is located adjacent the entrance of the cavitation chamber. The apparatus may further include a blade, such as a knife-like blade, disposed inside the mixing and/or cavitation chamber opposite the orifice component. In one version of such an embodiment, at least some of the portions of the orifice component surrounding the orifice and/or the blade are made of a material or materials that have a Vickers hardness of greater than or equal to about 20 GPa. A process for mixing by producing shear and/or cavitation in a fluid is also contemplated herein.

27 Claims, 5 Drawing Sheets

(56) References Cited

U.S. PATENT DOCUMENTS

| | | | |
|---|---|---|---|
| 3,658,302 A * | 4/1972 | Duthion et al. | 366/119 |
| 3,687,369 A * | 8/1972 | Johnstone | 239/381 |
| 3,926,413 A * | 12/1975 | D'Urso | 366/119 |
| 3,975,248 A * | 8/1976 | Gorman | 204/157.62 |
| RE29,161 E * | 3/1977 | Duthion et al. | 366/114 |
| 4,129,387 A * | 12/1978 | Grange et al. | 366/119 |
| 4,352,571 A * | 10/1982 | Grange et al. | 366/127 |
| 4,510,120 A * | 4/1985 | Bauer | 422/133 |
| 4,675,194 A | 6/1987 | Gaffney | |
| 5,026,167 A | 6/1991 | Berliner, III | |
| 5,143,965 A * | 9/1992 | Mertz | 524/436 |
| 5,154,347 A * | 10/1992 | Vijay | 239/4 |
| 5,695,510 A | 12/1997 | Hood | 606/169 |
| 5,837,272 A | 11/1998 | Fierro, Jr. et al. | |
| 5,975,750 A * | 11/1999 | Semp et al. | 366/119 |
| 6,290,331 B1 * | 9/2001 | Agarwal et al. | 347/47 |
| 6,331,314 B1 | 12/2001 | Klinksiek et al. | |
| 6,375,635 B1 * | 4/2002 | Moutafis et al. | 604/43 |
| 6,530,684 B1 * | 3/2003 | Kolb et al. | 366/176.1 |
| 6,749,329 B2 * | 6/2004 | Shechter et al. | 366/101 |
| 6,824,086 B1 * | 11/2004 | Mazurkiewicz et al. | 241/5 |
| 2002/0054995 A1 * | 5/2002 | Mazurkiewicz | 428/364 |
| 2004/0074979 A1 * | 4/2004 | McGuire | 239/1 |
| 2006/0109738 A1 | 5/2006 | Bucholz | |
| 2006/0159561 A1 * | 7/2006 | Tessien | 417/313 |
| 2008/0251375 A1 * | 10/2008 | Hielscher et al. | 204/157.42 |
| 2009/0003123 A1 * | 1/2009 | Morrison et al. | 366/76.1 |
| 2009/0087683 A1 * | 4/2009 | Shiraishi et al. | 428/800 |
| 2009/0258582 A1 * | 10/2009 | Miller | 451/102 |
| 2010/0020631 A1 * | 1/2010 | Gansmuller et al. | 366/137.1 |
| 2010/0273898 A1 * | 10/2010 | Enomura | 516/53 |
| 2010/0319785 A1 * | 12/2010 | Endmura | 137/14 |

* cited by examiner

APPARATUS AND METHOD FOR MIXING BY PRODUCING SHEAR AND/OR CAVITATION, AND COMPONENTS FOR APPARATUS

CROSS REFERENCE TO RELATED APPLICATION

This application claims the benefit of the filing date of U.S. Patent Application No. 60/937,501, filed Jun. 28, 2007.

FIELD OF THE INVENTION

The present invention is directed to an apparatus and method for mixing by producing shear and/or cavitation, and components for the apparatus.

BACKGROUND OF THE INVENTION

Cavitation refers to the process of forming partial vacuums within an unfilled space in a liquid. This can be done in a number of manners, such as through the use of a swiftly moving solid body (as an impeller), hydrodynamically, or by high-frequency sound waves.

Apparatuses and methods for producing cavitation are described in U.S. Pat. Nos. 3,399,031; 4,675,194; 5,026,167; and 5,837,272. One particular apparatus for producing hydrodynamic cavitation is known as a SONOLATOR® high pressure homogenizer, which is manufactured by Sonic Corp. of Stratford, Conn., U.S.A. The SONOLATOR® high pressure homogenizer directs liquid under pressure through an orifice into a chamber having a knife-like blade therein. The liquid is directed at the blade, and the action of the liquid on the blade causes the blade to vibrate at sonic or ultrasonic frequencies. This produces hydrodynamic cavitation in the liquid in the area around the blade.

The SONOLATOR® high pressure homogenizer has been in use for many years, and has been used as an in-line system, single or multi-feed, to instantly create fine, uniform and stable emulsions, dispersions, and blends in the chemical, personal care, pharmaceutical and food and beverage industries.

It has been found, however, that while such a high pressure homogenizer works well at certain pressures, the use of such an apparatus is limited above certain pressures (e.g., greater than or equal to about 1,000 psi (about $7 \times 10^6$ Pascals)), particularly when run continuously at such pressure. The limited use is due to high blade wear and corrosion. Blade wear can even occur at a pressure lower than 1,000 psi. (for example, at a pressure greater than or equal to about 500 psi. (about $3.4 \times 10^6$ Pascals)) over shorter time periods if the liquid contains solids, particularly solid crystals. In addition to blade wear, the pressurized fluid may cause both erosion and corrosion to take place at the orifice, thus, further deteriorating the overall performance of the apparatus.

The search for improved apparatuses and methods for mixing by producing shear and/or cavitation, and components for such apparatuses has, therefore, continued. In particular, it is desirable for apparatuses and methods for mixing by producing shear and/or cavitation to be developed that overcome the aforementioned problems. The search has led to the development of vibratable blades for those apparatuses that utilize blades, which have improved vibration characteristics.

SUMMARY OF TUE INVENTION

The present invention is directed to an apparatus and method for mixing by producing shear and/or cavitation, and components for the apparatus. There are numerous non-limiting embodiments of the present invention.

In one non-limiting embodiment, an apparatus for mixing by producing shear and/or cavitation is disclosed. The apparatus comprises, as its basic components: a mixing and/or cavitation chamber having an entrance, at least one inlet, and an outlet; and an element with an orifice therein located adjacent the entrance of the mixing and/or cavitation chamber. The element with the orifice therein comprises portions surrounding the orifice, and at least some of the portions surrounding the orifice may be formed of at least one material which has a hardness that is greater than at least one of: the hardness of cemented tungsten carbide, or a Vickers hardness of greater than or equal to about 20 GPa. The portions surrounding the orifice may, for instance, have a Vickers hardness between about 20 and about 100 or more GPa, or alternatively between about 30 and about 95 GPa, or alternatively between about 60 and about 95 GPa, or any narrower range that falls within these ranges. For convenience, the level or hardness and the ranges contained in this paragraph may be referred to as "the hardness ranges". The apparatus may further comprise at least one blade disposed in the mixing and/or cavitation chamber opposite the element with an orifice therein. The blade, or at least the leading edge of the blade, may be formed of at least one material which has a Vickers hardness in the hardness ranges specified above.

In other embodiments, the element with the orifice therein need not have a hardness in the hardness ranges specified above. For example, in other embodiments, the element with the orifice therein can have portions surrounding the orifice with a Vickers hardness of less than about 20 GPa, and the blade, or at least the leading edge of the blade, can be provided with a Vickers hardness in the hardness ranges specified above. In some embodiments, such blades may have improved vibration characteristics.

A process for mixing by producing shear and/or cavitation in a fluid is also described herein.

BRIEF DESCRIPTION OF THE DRAWINGS

The following detailed description will be more fully understood in view of the drawings in which.

The embodiments shown in the drawings are illustrative in nature and are not intended to be limiting of the invention defined by the claims. Moreover, individual features of the drawings and the invention will be more fully apparent and understood in view of the detailed description.

DETAILED DESCRIPTION

The present invention is directed to an apparatus and method for mixing by producing shear and/or cavitation, and components for the apparatus. It should be understood that, in certain embodiments, the ability of the apparatus and method to induce shear may not only be useful for mixing, but may also be useful for dispersion of solid particles in liquids and in breaking up solid particles. In certain embodiments, the ability of the apparatus and method to induce shear and/or produce cavitation may also be useful for droplet and/or vesicle formation.

Figure 1:
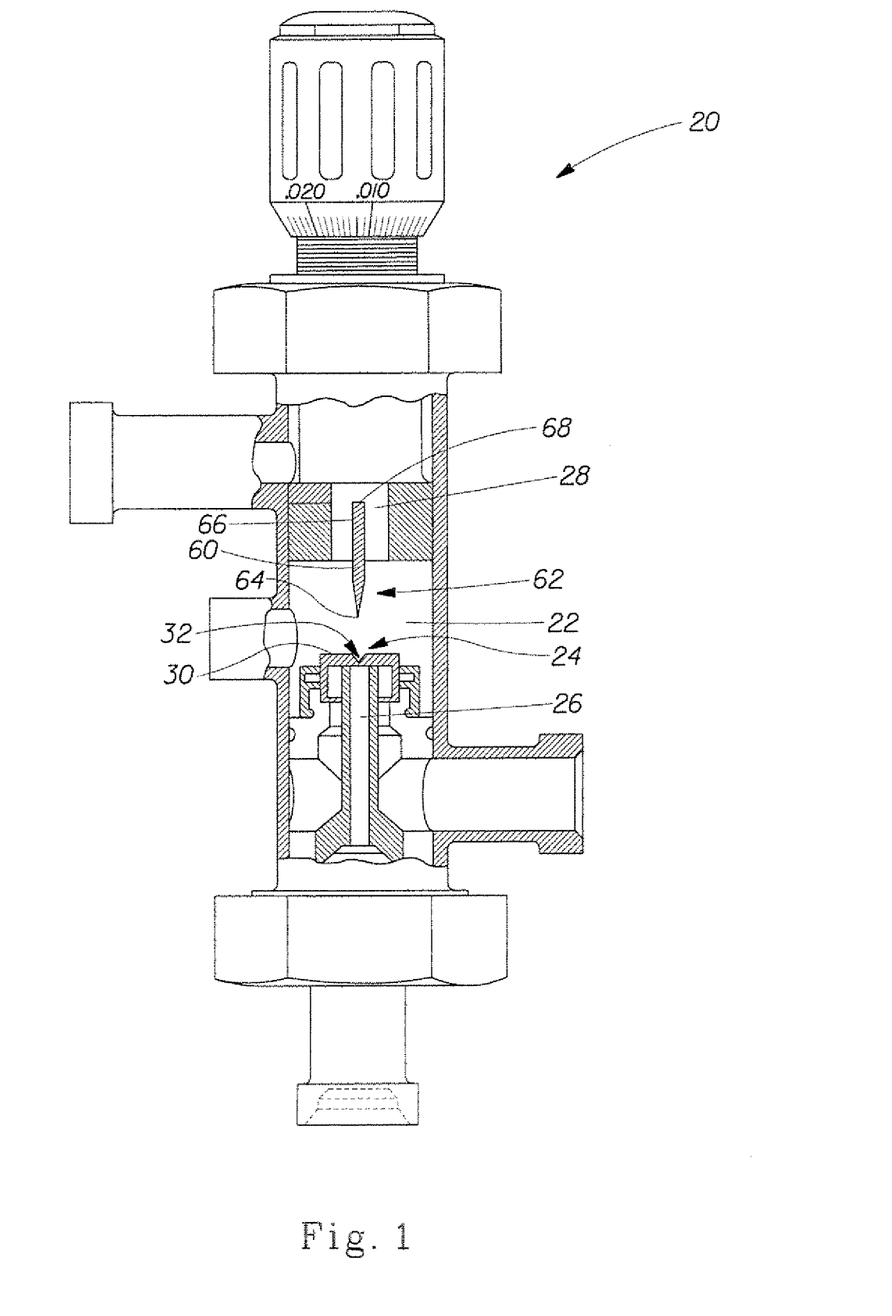
FIG. 1 is a partially fragmented cross-sectional view of one embodiment of an apparatus for mixing by producing shear and/or cavitation.

FIG. 1 shows one non-limiting embodiment of an apparatus 20 for mixing by producing shear and/or cavitation. As shown in FIG. 1, the apparatus 20 comprises: a mixing and/or cavitation chamber 22 which comprises an entrance 24, at least one inlet 26 and an outlet 28; and an element 30 or structure such as an orifice component with an orifice 32 therein. The element 30 is located adjacent the entrance 24 of the mixing and/or cavitation chamber 22. The apparatus 20 may further comprise a blade 60, such as a knife-like blade, disposed in the mixing and/or cavitation chamber 22 opposite the element 30 with an orifice 32 therein.

The apparatus 20 can comprise a SONOLATOR® high pressure homogenizer available from Sonic Corp. of Stratford, Conn., U.S.A. as shown; or, in other embodiments a Gaulin homogenizer available from Invensys APV, Lake Mills, Wis., U.S.A.; a MICROFLUIDIZER® fluid material processor available from Microfluidics Corp. of Newton, Mass., U.S.A.; an atomizer; or, any other suitable apparatus. SONOLATOR® high pressure homogenizers are described in the U.S. Pat. No. 3,176,964 issued to Cottell, et al. and U.S. Pat. No. 3,926,413 issued to D'Urso. Although the following discussion is expressed primarily in terms of the components for the SONOLATOR® high pressure homogenizer, it should be understood that the materials described herein can be used for the parts that are subject to wear in any type of high pressure mixing or homogenizing device, including but not limited to the valve and/or disk used in other high pressure homogenizers. In some embodiments, it may be desirable for the apparatus described herein, and the components thereof, to exclude those used in water jet cutting devices and sand blasting devices. Thus, it is desirable for the apparatus to be capable of mixing the materials that are fed into the apparatus, rather than merely spraying water. This mixing can take place inside a mixing chamber, such as the cavitation chamber 22.

Figure 2:
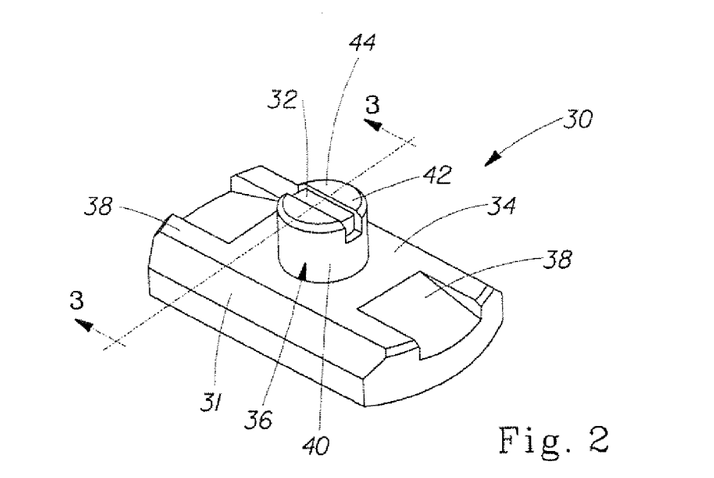
FIG. 2 is an enlarged perspective view of one embodiment of an element with an orifice therein for use in the apparatus shown in FIG. 1.

The element 30 with the orifice 32 therein can be in any suitable configuration. In the embodiment shown in FIG. 2, the element 30 comprises a housing 31 comprising a plate-like portion 34 with a protuberance 36 in the central region of the plate-like portion 34. The plate-like portion 34 defines sides or wings 38 to the side of the protuberance 36. FIG. 2 shows that the protuberance 36 comprises side walls 40 having a top or front surface 42 joined thereto. The front surface 42 of the protuberance 36 has the orifice 32 formed therein and portions 44 surrounding the orifice 32.

The term "joined", as used in this specification, encompasses configurations in which an element is directly secured to another element by affixing the element directly to the other element; configurations in which the element is indirectly secured to the other element by affixing the element to intermediate member(s) which in turn are affixed to the other element; and configurations in which one element is integral with another element, i.e., one element is essentially part of the other element.

The orifice 32 can be in any suitable configuration. Suitable configurations include, but are not limited to: slot-shaped, eye-shaped, elliptically-shaped, triangular, square, rectangular, in the shape of any other polygon, or circular. In some embodiments, as shown in FIG. 2, it may be desirable for the width of the orifice to exceed the height of the orifice. The width of the orifice 32 may be any multiple of the height of the orifice including, but not limited to: 1.1, 1.2, 1.3, 1.4, 1.5, 2, . . . , 2.5, 3, 3.5, . . . , etc. up to 100 or more times the height of the orifice. The orifice 32 can be of any suitable width including, but not limited to, up to about 1 inch (2.54 cm), or more. The orifice 32 can have any suitable height including, but not limited to, up to about 0.5 inch (about 1.3 cm), or more.

Figure 3:
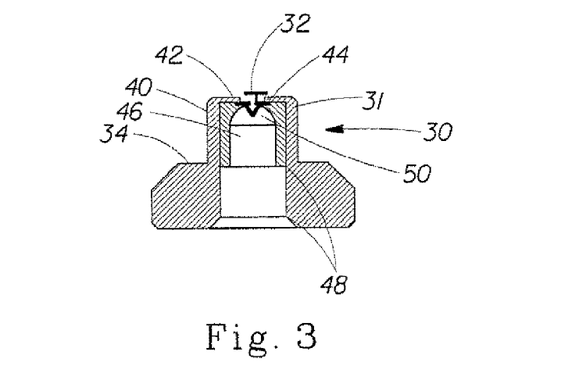
FIG. 3 is a cross-section of the element shown in FIG. 2 taken along line 3-3 of FIG. 2.
Figure 5:
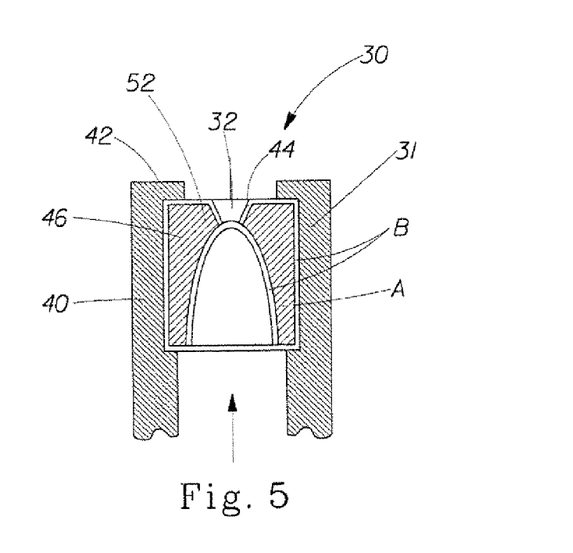
FIG. 5 is a simplified fragmented schematic cross-sectional view taken from an angle similar to that of FIG. 3 showing an orifice component comprising a composite of different materials.

FIG. 3 shows that the element 30 with the orifice 32 therein can comprise one or more components or an orifice component system. For example, in the embodiment shown in FIG. 3, the element 30 with the orifice 32 therein comprises a housing 31 with a hollow protuberance 36, and the hollow protuberance 36 has an insert 46 therein. The insert 46 can be in any suitable configuration. In the embodiment shown in FIG. 3, the insert 46 is a bullet-shaped element that has one or more flange portions 48 at the mid-portion and/or rear part of the insert 46. The insert 46 has an interior passageway for transport of liquid therethrough and a nozzle portion 50 at the front of the insert. This interior passageway is shown in greater detail in FIG. 5. FIG. 5 also shows that the portions 4 surrounding the orifice 32 form a wall 52 that becomes thinner in at least some places as the orifice 32 is approached. Numerous other configurations for the insert 46 are possible including, but not limited to flat, plate-like configurations. The insert 46 may be made of a harder material than other portions or components of the structure comprising the element 30. The insert 46 is used so that the other larger portions or components of the element 30 can be made from a less hard, and less expensive material.

The element 30, and the components thereof, can be made of any suitable material or materials. Suitable materials include, but are not limited to: titanium, stainless steel, tool steel, cemented tungsten carbide, ceramics (including oxide ceramic materials and non-oxide ceramic materials), silicon nitride ($Si_3N_4$), titanium nitride (TiN), aluminum oxide ($Al_2O_3$) (which in single crystal form is known as sapphire), silicon carbide (SiC), titanium carbide (TiC), boron carbide ($B_4C$), titanium diboride ($TiB_2$), boron oxide ($B_6O$), cubic boron nitride (cBN) (including polycrystalline cBN and epitaxially-grown cBN), cubic $BC_2N$, diamond-like carbon (DLC), diamond (e.g., bulk diamond) (natural and synthetic), composites of diamond and/or cubic boron nitride, and coatings of any of the above materials, including but not limited to diamond-coated materials (polycrystalline diamond-coated materials and epitaxially-grown diamond coatings) and diamond-like carbon. Other suitable materials include combinations of incompressible transition metals, which are relatively soft (such as osmium, rhenium, and ruthenium), with small covalent main group elements having short bonds (such as boron, carbon, nitrogen, or oxygen) to make the metals hard, producing materials such as osmium diboride ($OsB_2$), rhenium diboride ($ReB_2$) and ruthenium diboride ($RuB_2$). Other materials potentially of interest include: osmium carbide (OsC), osmium nitride (OsN), osmium dioxide ($OsO_2$), rhenium carbide (ReC), rhenium nitride (ReN), rhenium dioxide ($ReO_2$), ruthenium carbide (RuC), ruthenium nitride (RuN), and ruthenium dioxide ($RuO_2$). Some of these materials may be formed in the absence of high pressure, making them more economical to produce. These latter materials are described in the following articles: R. W. Cumberland, et al., "Osmium diboride, an ultra-incompressible, hard material", J. Am. Chem. Soc., 127, 7264 (2005); R. B. Kaner, et al. "Designing superhard materials", Science, 308, 1268 (2005); H. Chung, et al. "Synthesis of Ultra-Incompressible Superhard Rhenium Diboride at Ambient Pressure", Science, Vol. 316, Apr. 20, 2007; and, "Materials, Taking a Super-hard Approach". R&D Magazine, May, 2007, published by Advantage Business Media, Rockaway, N.J., U.S.A.

The Vickers hardness $H_v$ of several of these materials are provided in Table 1 below. According to J. Mater. Res. Vol. 17, No. 12, December 2002, Materials Research Society, materials with a Vickers hardness greater than or equal to 40 GPa are considered to be superhard materials.

TABLE 1

Vickers Hardness of Various Materials

| Material | Approximate Vickers hardness Giga Pascals (Gpa) |
|---|---|
| Tool steel | 4.5-6.5 |
| Cemented Carbide Tooling[1] | 11-19 |
| Silicon Nitride ($Si_3N_4$) | 22 |
| Titanium Nitride (TiN) | 22-31 |
| Aluminum Oxide ($Al_2O_3$) (Sapphire) | 23 |
| Silicon Carbide (SiC) | 28 |
| Boron Carbide ($B_4C$) | 30 |
| Titanium Diboride ($TiB_2$) | 32 |
| Boron Oxide ($B_6O$) | 35 |
| Rhenium Diboride ($ReB_2$) | 30-48 |
| Cubic Boron Nitride (cBN) | 62 |
| Cubic $BC_2N$ | 75 |
| Diamond | 95 |

[1]Microhardness Material Hardness Measurement, http://www.brycoat.com/hardness.htm
All Vickers hardness values specified in the appended claims are measured according to ASTM Standard E92-72.

In the embodiment shown in FIGS. 2 and 3, the element 30 comprises a housing 31 and an insert 46. In such an embodiment, it may be desirable for at least the nozzle portion 50 at the front of the insert 46 to be made of a material having a Vickers hardness of greater than or equal to about 20 GPa because this is the portion of the orifice component system that is subject to the greatest forces when liquids and/or other material is sprayed through the nozzle portion 50. Alternatively, it may be desirable for the entire insert 46 to be made of a material having a hardness in the hardness ranges specified above. In other embodiments, where there is a single component orifice component system (that is, with no separate insert), it may be desirable for at least the portions 4 surrounding the orifice 32 (which would be subjected to the greatest forces) to be made of a material having a hardness in the hardness ranges specified above.

Thus, in certain non-limiting embodiments, the portions 44 of the element 30 surrounding the orifice 32 may be provided with a Vickers hardness of greater than or equal to about 20 GPa. The portions 44 surrounding the orifice 32 may be provided with a Vickers hardness in any increment of 1 Vickers hardness unit above 20 GPa. In other embodiments, all or a portion of any of the components of the orifice component system can be made out of one of the materials described herein, and at least some of such components can be partially or entirely coated with a material described herein which has a higher hardness.

Materials having a Vickers hardness of greater than or equal to about 20 GPa which are useful herein include, but are not limited to: silicon nitride, titanium nitride, aluminum oxide, silicon carbide, titanium carbide, boron carbide, titanium diboride, boron oxide, rhenium diboride, cubic boron nitride, cubic $BC_2N$, diamond-like carbon, diamond (e.g., bulk diamond) (natural and synthetic), and composites of diamond and/or cubic boron nitride, and coatings of any of the above materials, including but not limited to diamond-coated materials and diamond-like carbon. Materials have also been theorized (e.g., carbon nitrite) which are expected by some people to have a hardness similar to that of diamond. Such materials, if and when they become available, may also be suitable for use herein. Several of these materials are described in greater detail below.

Cubic boron nitride (cBN) is a synthetic material, which is available both in bulk form (as a polycrystalline structure and as a single crystal), and in the form of coatings (polycrystalline coatings and epitaxially-grown coatings).

Diamond like carbon (DLC) is characterized by both SP2 and SP3 bond structures, and as a result, tends to be amorphous. Diamond like carbon is typically only available in the form of coatings (rather than bulk form), and is highly wear resistant, and very stable chemically against erosion and corrosion.

Natural and synthetic diamonds are characterized by SP3 bond structures. Synthetic (man-made) diamond include polycrystalline diamond (PCD) and single crystal diamond, and coatings. Polycrystalline diamond (PCD) can include bulk diamond, which comprises a three-dimensional structure of many crystals that are sintered together, and polycrystalline diamond coatings that are deposited on an appropriate substrate.

Composites of diamond and cBN typically comprise composites of polycrystalline diamond (PCD) and a polycrystalline cBN. The polycrystalline diamond (PCD) used in such composites can be natural or synthetic. Suitable composites can comprise any suitable proportions of PCD and cBN, from 1-99% PCD to 1-99% cBN. Composites of diamond and cBN are typically formed at high temperature and high pressure by sintering particles of polycrystalline diamond (PCD) and cBN together with binders such as nickel, cobalt, or iron.

Figure 9:
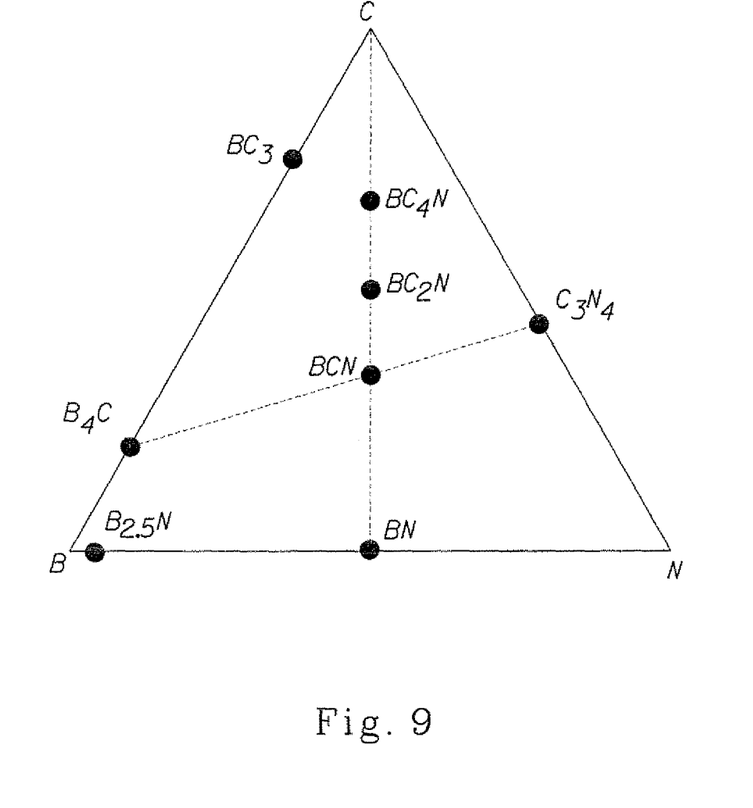
FIG. 9 is the Ternary B—C—N (boron-carbon-nitrogen) phase diagram.

In addition, appropriate materials having a hardness in the hardness ranges specified above can comprise any other materials falling within the scope of the Ternary B—C—N (boron-carbon-nitrogen) phase diagram shown in FIG. 9.

The element 30, and the components thereof can be formed in any suitable manner. Any of the components of the orifice component system 30 can be formed from solid pieces of the materials described above which are available in bulk form. The components may also be formed of a solid piece of one of the materials specified above, which is coated over at least a portion of its surface with one or more different materials specified above. In these embodiments, or in other embodiments, the orifice component system 30 can be formed from more than one piece. In this latter case, the different pieces can be formed from different materials. For example, in one embodiment, the orifice 32 can be provided in an insert, such as insert 46, that is cut out of a diamond using a laser or hot wire diamond cutter, diamond-based cutting tools, and optionally polished using diamond dust. This insert 46 can be inserted into or joined to a metal piece that forms the rest of the orifice component system, such as the housing 31. In other cases, the entire element 30, including the housing 31 can be made of bulk diamond, and there need not be an insert.

FIG. 5 shows one example of an embodiment in which a portion of at least one of the components of the element 30 is made out of one of the materials described herein, and this portion can be partially or entirely coated with a material described herein which has a higher hardness. For instance, the inner portion, A, comprising the insert 46 of the element 30 can be made of: steel, titanium, or cemented tungsten carbide, and the outer portion B thereof can comprise a coating of cubic boron nitride (cBN) (in the form of either polycrystalline coatings and epitaxially grown coatings), or a diamond coating. These and other suitable combinations of materials for such a composite structure are listed in Table 2 below.

In other embodiments, the element 30 with the orifice 32 therein need not have a hardness at the level specified above. For example, in other embodiments, the element 30 with the orifice 32 therein can have portions surrounding the orifice 32 with a Vickers hardness of less than about 20 GPa.

Figure 4:
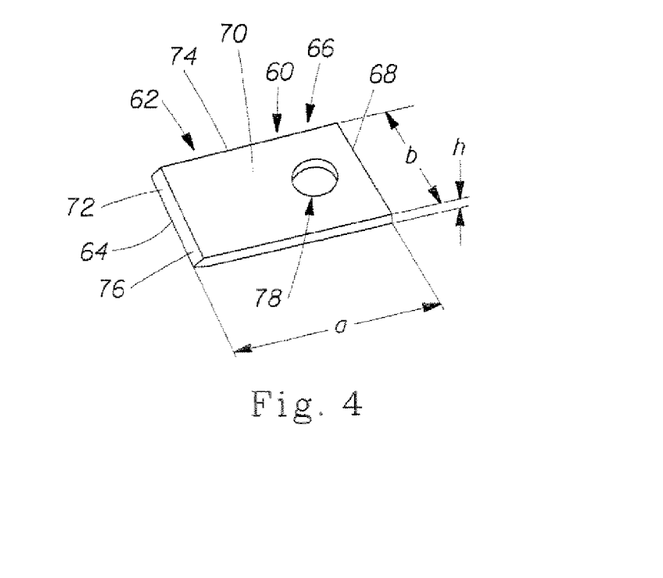
FIG. 4 is an enlarged perspective view of one embodiment of a blade for use in the apparatus shown in FIG. 1.

In some cases, it is desirable for the apparatus for mixing by producing shear and/or cavitation to comprise a blade 60. A blade 60 may be used, for example, if it is desired to use the apparatus 20 to form emulsions with a lower mean droplet size than if the blade was not present. As shown in FIG. 1, the blade 60 has a front portion 62 comprising a leading edge 64, and a rear portion 66 comprising a trailing edge 68. As shown in FIG. 4, the blade 60 also has an upper surface 70, a lower surface 72, and a thickness, h, measured between the upper and lower surfaces. In addition, the blade 60 has a pair of side edges 74 and a width, b, measured between the side edges 74.

The blade 60 can have any suitable configuration. As shown in FIG. 4, the blade can comprise a tapered portion 76 in which the thickness of the blade increases from the leading edge 64 in a direction from the leading edge 64 toward the trailing edge 68 along a portion of the distance between the leading edge 64 and the trailing edge 68. The blade 60 shown in FIG. 4 has a single tapered or sharpened edge forming its leading edge 64. It should be understood that in other embodiments, the blade 60 may have two, three, or four or more tapered or sharpened edges. For example, the blade 60 can have a rectangular, or square configuration, and any or all of its sides can be sharpened. Such a configuration may be useful so that the blade 60 can be inserted into the apparatus 20 with any of the sharpened edges oriented to form the leading edge 64 of the blade 60. This will multiply the useful life of the blade before it is necessary to repair the same.

The blade 60 can have any suitable dimensions. In certain embodiments, the blade 60 can range in size from as small as 1 mm long and 7 microns thick to as big as 50 cm long and over 100 mm thick. One non-limiting example of a small blade is about 5 mm long and 0.2 mm thick. A non-limiting example of a larger blade is 100 mm long and 100 mm thick.

As shown in FIG. 1, when the blade 60 is inserted into the apparatus 20, a portion of the rear portion of the blade 60 is clamped, or otherwise joined inside the apparatus so that its position is fixed. The blade 60 can be configured in any suitable manner so that it can be joined to the inside of the apparatus. As shown in FIG. 4, in one non-limiting embodiment, the rear portion 66 of the blade 60 has at least one hole 78 therein for receiving a structure that passes through the hole. This hole and structure serves as at least pan of the mechanism used to retain the blade 60 in place inside the apparatus 20. The blade 60 can also be joined to a holder which may be comprised of metal or another suitable material. The remainder of the blade 60, including the front portion 62 of the blade 60, is free and is cantilevered relative to the fixed portion.

The blade 60 can comprise any suitable material or materials. The blade desirably will comprise a material or materials, that are chemically compatible with the fluids to be processed. (The same may also be desirable for the components of the orifice component system.) It may be desirable for the blade to be comprised at least partially of a material that is chemically resistant to one or more of the following conditions: low pH's (pH's below about 5); high pH's (pH's above about 9); salts (chloride ions); and oxidation.

Suitable materials for the blade 60 include, but are not limited to any material or materials described herein as being suitable for use in the orifice component system, and the components thereof. It should be understood, however, that the materials specified herein do not necessarily have all of the desired chemical resistance properties. The entire blade 60 may be comprised of one of the above materials.

Alternatively, a portion of the blade 60 may comprise one of the materials described herein as being suitable for use in the orifice component system, and another portion (or portions) of the blade 60 may comprise a different one of these materials. For example, in some cases, it may be desirable for a portion of the blade, such as the tapered portion 76, to comprise a harder material than the remainder of the blade 60. This may be desirable since the tapered portion 76 forms the leading edge 74 of the blade 60 and will be the portion of the blade subject to greatest wear during use. The remainder of the blade 60 can be comprised of some other material, such as a material that has one or more of the following properties: is less hard, less expensive, more ductile, or less brittle than the tapered portion 76.

Table 2 shows non-limiting examples of many of the different possible combinations of materials that can be used to construct one or more components of an element 30, or a composite blade 60. The letter "A" in Table 2 represents a portion of one or more components of the element 30, or a composite blade 60 structure shown in FIGS. 5 and 6, respectively, that may be referred to as an "inner" portion or structure, and the letter "B" represents a component of the composite structure that may be referred to as an "outer" portion or coating. In one non-limiting example, the inner portion A of the blade 60 could comprise sintered PCD which has a diamond coating, B, formed by chemical vapor deposition.

Figure 6:
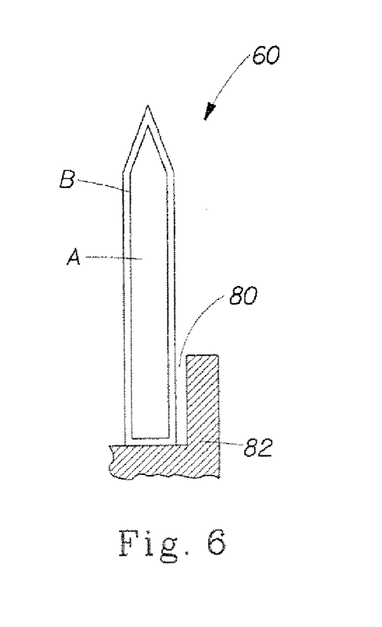
FIG. 6 is a simplified cross-sectional view of a blade shown in a partially fragmented holder for the same in which the blade comprises a composite of different materials.

As shown in FIG. 6, it may further be desirable for the apparatus 20 to be provided with dampening material 80 between the blade 60 and the structure 82 to which the blade 60 is clamped. Material suitable for dampening includes, but is not limited to rubber, TEFLON® material, and indium foil.

Figure 6A:
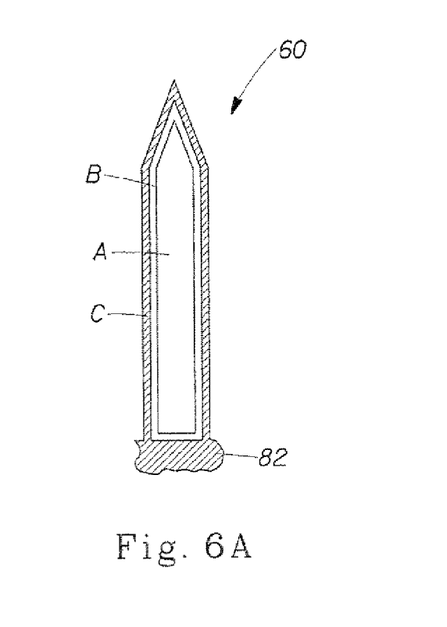
FIG. 6A is a simplified cross-sectional view similar to FIG. 6 showing another embodiment of a blade comprising a composite of different materials.

As shown in FIG. 6A, it is also possible to provide more than one coating on all or a portion of the surfaces of the components of the orifice component system 30 or the blade 60. The blade 60 shown in FIG. 6A has a coating B thereon, and additionally has a second coating, C, disposed on the coating B. In this case, the coating B forms an intermediate coating. There can be any suitable number of coatings on the components of the composite orifice component system 30, or the composite blade 60. The coatings B and C can both comprise the same material; or, they may comprise any different materials described herein as being suitable for application in the form of coatings. Such additional coatings can be provided for any suitable purpose. For instance, if the coating C has the hardness desired, but it is not chemically or thermally compatible with the material forming the inner portion A, it may be desirable to form an intermediate coating B that is compatible with the material forming the inner portion A and the material of coating C so that coating C can be properly joined to the inner portion A.

In addition, any of the structures described herein can be repaired with any of the coatings described herein. For example, if a component of the orifice component system 30 or the blade 60 degrades through wear, it is possible to repair the worn component or blade with the coatings described herein (such as repairing the same with a diamond coating formed by chemical vapor deposition).

TABLE 2

Combinations of Materials in Composite Orifice and Blade Structures

| Component A | Component B |
| --- | --- |
| Titanium | Silicon nitride, titanium nitride, aluminum oxide, silicon carbide, titanium carbide, boron carbide, titanium diboride, boron oxide, cubic boron nitride (cBN), cubic $BC_2N$, diamond-like carbon (DLC), diamond, and coatings of any of the above materials, including but not limited to diamond-coated materials (polycrystalline diamond-coated materials and epitaxially-grown diamond coatings), diamond-like carbon, and composites of diamond and cubic boron nitride |
| Stainless steel | Same as above |
| Tool steel | Same as above |
| Cemented Carbide Tooling | Same as above |
| Silicon Nitride ($Si_3N_4$) | Same as above, except silicon nitride |
| Titanium Nitride (TiN) | Same as above, except silicon nitride and titanium nitride |
| Aluminum Oxide ($Al_2O_3$) (Sapphire) | Same as above, except silicon nitride, titanium nitride, and aluminum oxide |
| Silicon Carbide (SiC) | Same as above, except silicon nitride, titanium nitride, aluminum oxide, and silicon carbide |
| Boron Carbide ($B_4C$) | Same as above, except silicon nitride, titanium nitride, aluminum oxide, silicon carbide, and boron carbide |
| Titanium Diboride ($TiB_2$) | Boron Oxide, Rhenium Diboride, Cubic Boron Nitride, Cubic $BC_2N$, and diamond |
| Boron Oxide ($B_6O$) | Rhenium Diboride, Cubic Boron Nitride, Cubic $BC_2N$, and diamond |
| Rhenium Diboride ($ReB_2$) | Cubic Boron Nitride, Cubic $BC_2N$, and diamond |
| Composites of Cubic Boron Nitride (cBN), Cubic $BC_2N$, and Diamond | Cubic Boron Nitride, Cubic $BC_2N$, and diamond |
| Cubic Boron Nitride (cBN) | Cubic $BC_2N$ and diamond |
| Cubic $BC_2N$ | Diamond |
| Diamond (single crystal and polycrystalline) | Diamond coating |

The blade 60, or various portions thereof, may have any suitable hardness. In one non-limiting embodiment, at least the tapered portion 76 of the blade 60 is formed from a material with a hardness in the hardness ranges specified above. In other embodiments, at least the tapered portion 76 of the blade 60 may be formed from a material with a Vickers hardness in any increment of 1 Vickers hardness unit above 20 GPa. In such embodiments, the remainder of the blade can comprise a material that has a Vickers hardness of less than 20 GPa. For instance, the tapered portion 76 of the blade 60 can be provided with a diamond coating, and the remainder of the blade 60 could be made of stainless steel.

Several non-limiting examples of methods of forming a blade 60 are described below. These include: forming a coated composite structure; forming a blade by coating layers of a material to form or build the final blade structure; and, forming a blade of a bulk material. The same techniques can be used to form components of the orifice component system, or components of other types of devices.

There are a number of methods of forming coated composite structures such as diamond coated structures, cBN coated structures, diamond composite coated structures, or structures coated with any of the other materials described herein which are capable of being applied in the form of coatings. Suitable methods include, but are not limited to: physical vapor deposition, chemical vapor deposition, and plasma deposition. In one non-limiting embodiment, a composite blade is formed from a stainless steel, titanium, or cemented tungsten carbide substrate that forms the interior of the blade, which is coated with a diamond coating, cBN, or diamond like carbon coating.

In another embodiment, a polycrystalline solid diamond blade 60 is made by coating a generally flat silicon single crystal substrate or wafer with diamond using plasma by conventional plasma deposition techniques, such as plasma chemical vapor deposition (CVD), or by hot filament deposition. In this method, the silicon substrate is initially seeded with small (approximately 1 micron in size) diamond nuclei by rubbing diamond paste or diamond powder onto the substrate. The diamond-coating approach can use saturated or non-saturated hydrocarbons, such as methane, acetylene, or ethylene in a hydrogen or in a noble gas (such as argon) environment and/or plasma environment to deposit the diamond-containing coating. The diamond-containing coating can be deposited layer-by-layer on the silicon substrate. After the thickness of diamond film reaches about 2 mm thick, the process is discontinued, and the silicon substrate can be removed. This process may be referred to as plasma-enhanced chemical vapor deposition (or "PECVD"). The silicon substrate can be removed by (wet or dry) etching, or by mechanical grinding. This will create a blade structure which is rough on both sides. The blade can be provided with a tapered leading edge by laser ablation and/or mechanical grinding. Chemical and/or mechanical means can then be used to polish the blade structure.

In other embodiments, the blade 60 can comprise a bulk material, such as bulk diamond material. Such a material can be formed in any suitable manner such as by high pressure and high temperature sintering in the presence of bonding elements such as cobalt, nickel, or iron using presses that form synthetic diamond from diamond dust. Forming the blade out of some materials, such as bulk diamond may be useful to provide the blade with more efficient acoustic vibration characteristics.

The acoustic properties may vary significantly from one material to another. Accordingly, the shape and size of the blade may need to differ depending on the material of the blade for a given resonant mode. Cavitation threshold (the minimum acoustic pressure at the onset of cavitation) is acoustic frequency dependent. At high ultrasonic frequencies, cavitation becomes increasingly more difficult. The maximum cavitation intensity occurs at low ultrasonic frequencies. It is desired to have the blade designed so that its resonant frequency is in the acoustic and low ultrasonic frequency range of from about 15 kHz to 100 kHz, or any narrower range of frequencies falling within such range including, but not limited to from about 18 Hz to 40 kHz.

The blade 60 is schematically illustrated as a rectangular plate in FIG. 4. Assuming (for simplicity) that the hole is not present, and one end 68 of the blade is clamped, and the other three sides are free. The plate has a length of a (from the clamping point), width of b and thickness of h. The natural frequency of the blade can be expressed as $$f_{ij} = \frac{k_{ij}^2}{2\pi a^2}\left[\frac{Eh^2}{12\rho(1-v^2)}\right]^{1/2} \qquad \text{Eq. 1}$$

where $f_{ij}$ is the resonant frequency at mode indices (i,j), i being the mode number in length, j being the mode number in width; $k_{ij}$ is a dimensionless frequency parameter; E is the modulus of elasticity, $\rho$ is the density, and $\upsilon$ is Poisson's ratio. As a compression wave, the wave velocity C can be expressed as $$C = \sqrt{\frac{E}{\rho}} \qquad \text{Eq. 2}$$

Substituting Eq. 2 to Eq. 1, the equation for resonant frequency becomes, $$f_{ij} = \frac{k_{ij}^2}{2\pi a^2} Ch\left[\frac{1}{12(1-v^2)}\right]^{1/2} \qquad \text{Eq. 3}$$

The mechanical properties of several superhard materials, and cemented tungsten carbide are set forth in Table 3 below for comparison. Cubic boron nitride and cubic $BC_2N$ (c-$BC_2N$) are superhard materials having a hardness close to that of diamond. These materials are similar to diamond in that they are all: isotropic (their properties are the same in all directions), covalently bonded, and, all their bonds are SP3 bonds. There are differences in the mechanical properties of these materials depending on whether the material is in polycrystalline or in single crystal structures. However, the magnitude of the difference due to the state of each material is relatively small compared to the differences in these properties between the materials. The mechanical properties listed in Table 3 below are the values in polycrystalline state, but the values are expected to approximate that of the single crystal state.

TABLE 3

Mechanical properties of the superhard materials: diamond, c-$BC_2N$ and cBN in comparison to cemented tungsten carbide.

| Material | Elastic modulus (GPa) | Density (gram/cm³) | Predicted Acoustic velocity (m/s) |
|---|---|---|---|
| Cemented Tungsten Carbide (94% WC + 6% Co) | 630 | 14.900 | 6,502 |
| Cemented Tungsten Carbide (75% WC + 25% Co) | 470 | 12.900 | 6,036 |
| cBN | 909 | 3.500 | 16,115 |
| c-$BC_2N$ | 980 | 3.358 | 17,083 |
| Diamond | 1141 | 3.512 | 18,024 |

Due to its high elastic modulus (>900 MPa) and relatively low bulk density (3.512 g/cm³), diamond has the fastest acoustic velocity at 18,024 m/s. This compares to titanium 6,070 m/s, stainless steel of 5,900 m/s, water of 1,500 m/s and air of 310 m/s.

It may be desirable for the blade 60 to have an elastic modulus of greater than or equal to about 700, 750, 800, 850, or 900 GPa. It may be desirable for the blade to have a density of less than or equal to about any of the following: 12, 10, 9, 8, 7, 6, 5, 4, or 3.6 g/cm³. It may be desirable for the blade 60 to have or be made from a material having a predicted acoustic velocity greater than or equal to about any of the following: 7,640, 8,000, 9,000, 10,000, 11,000, 12,000, 13,000, 14,000, 15,000, or 16,000 m/s.

Figure 7:
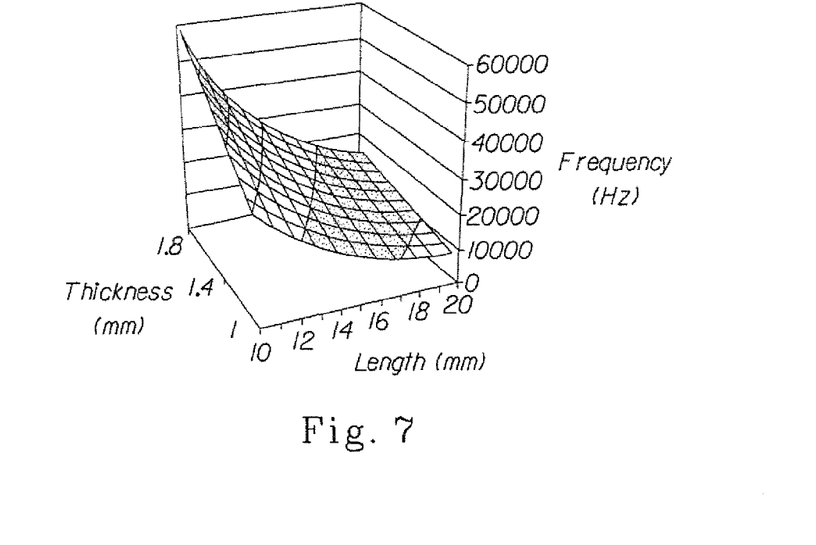
FIG. 7 is a three dimensional graph showing the resonant frequency of a diamond blade as a function of blade thickness and length.
Figure 8:
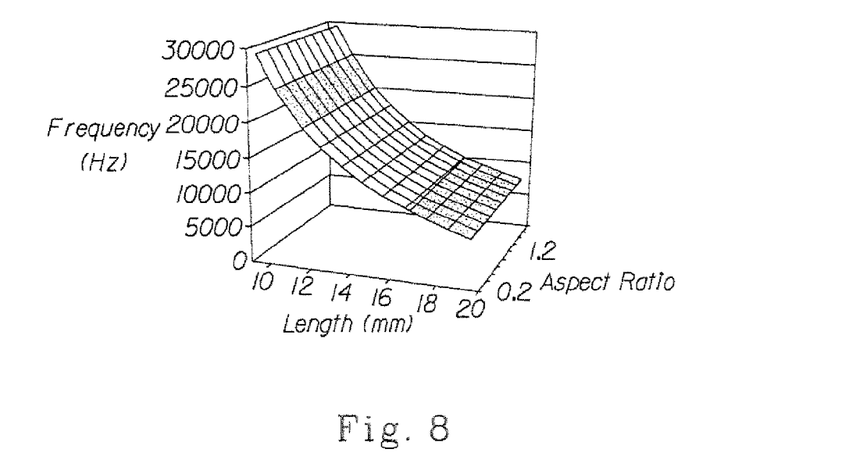
FIG. 8 is a three dimensional graph showing the resonant frequency of a diamond blade as a function of blade thickness and aspect ratio (length/width).

The formulas and properties provided above allow various characteristics of the blade 60 to be modeled, to apply to blades made from different materials. The modeling defines a range of combinations of blade thickness and length which give the blade the desired resonant frequency. FIG. 7 shows the frequency of a blade made of bulk diamond as a function of blade thickness and length. As shown in FIG. 8, unlike blades made from other materials, in the case of blades made from certain superhard materials (particularly those having low densities like diamond), the aspect ratio (ratio of blade length to blade width) has been found to have little impact on the resonant mode. In other words, the blade can be made narrow or wide, with little impact on the resonant frequency. This enables the blade to be made relatively wide without changing the length of the blade. This can provide the advantage of allowing increased flow rates to be handled by the apparatus by merely increasing the widths of the orifice and the blade, without changing the length, or thickness of the blade.

A process for mixing by producing shear and/or cavitation in a fluid is also contemplated herein. In one non-limiting embodiment, the process utilizes an apparatus 20 such as that described above. The process comprises providing a mixing or cavitation chamber, such as 22, and an element 30, such as orifice component system, with an orifice 32 therein. The element 30 comprises portions 44 surrounding the orifice 32, and the portions 44 surrounding the orifice 32 may be provided with a hardness in the hardness ranges specified above.

The process further comprises introducing at least one fluid into at least one entrance to the mixing or cavitation chamber 22 so that the fluid passes through the orifice 32 in the element 30. The at least one fluid can be supplied to the apparatus 20 in any suitable manner including, but not limited to through the use of pumps and motors powering the same. The pumps can supply at least one fluid to the apparatus under the desired pressure. There can be any suitable number of inlets, such as 26, to the cavitation chamber (e.g., 1, 2, 3, 4, 5, etc.) The fluid(s), or the mixture of the fluids, pass through the orifice 32 under pressure. The orifice 32 is configured, either alone, or in combination with some other component, to mix the fluids and/or produce cavitation in the fluid(s), or the mixture of the fluids.

The fluid can comprise any suitable liquid or gas. In some embodiments, it may be desirable for the fluid to comprise two or more different phases, or multiple phases. The different phases can comprise one or more liquid, gas, or solid phases. In the case of liquids, it is often desirable for the liquid to contain sufficient dissolved gas for cavitation. Suitable liquids include, but are not limited to: water, oil, solvents, liquefied gases, slurries, and melted materials that are ordinarily solids at room temperature. Melted solid materials include, but are not limited to waxes, organic materials, inorganic materials, polymers, fatty alcohols, and fatty acids.

The fluid(s) can also have solid particles therein. The particles can comprise any suitable material including, but not limited to: $TiO_2$, bismuth containing materials, ZnO, $CaCO_3$, $Na_2SO_4$, and $Na_2CO_3$. The particles can be of any suitable size, including macroscopic particles and nanoparticles. In some cases, at least some of these solid particles may be amorphous. In some cases, at least some of these solid particles may be crystalline. In some cases, at least some of the solid particles may be abrasive.

These particles may be present in any suitable amount in the liquid. Suitable amounts may fall within any suitable range, including but not limited to between about 0.01% to about 40% or more; alternatively between about 0.1% to about 10%; or, alternatively between about 0.5% and about 4% by weight.

The process may further comprise providing a vibratable blade, such as blade 60, disposed in the mixing or cavitation chamber 22 opposite the element 30 with an orifice 32 therein. The blade 60 may be provided with a hardness in the hardness ranges specified above. In cases where a blade 60 is used, the process may include a step of forming the liquid into a jet stream and impinging the jet stream against the vibratable blade with sufficient force to induce the blade to vibrate harmonically at an intensity that is sufficient to generate cavitation in the fluid. The cavitation may be hydrodynamic, acoustic, or ultrasonic. In some embodiments, the blade 60 undergoes harmonic ultrasonic vibration at a frequency of from about 15 kHz to about 100 kHz.

The process may be carried out under any suitable pressure. In certain embodiments, the pressure as measured at the feed to the orifice immediately prior to the point where the fluid passes through the orifice is greater than or equal to about 500 psi., or any number greater than 500 psi. including, but not limited to: 1,000, 1,500, 2,000, 2,500, 3,000, 3,500, 4,000, 4,500, 5,000, 5,500, 6,000, 6,500, 7,000, 7,500, 8,000, 8,500, 9,000, 9,500, 10,000 psi., and any 500 psi. increment above 10,000 psi., including 15,000, 20,000, or higher.

A given volume of fluid can have any suitable residence time within the cavitation chamber. Some suitable residence times include, but are not limited to from about 1 millisecond to about 1 second, or more. The fluid(s) can flow at any suitable flow rate through the cavitation chamber. Suitable flow rates range from about 1 to about 1,000 L/minute, or more, or any narrower range of flow rates falling within such range including, but not limited to from about 5 to about 1,000 L/min.

The process may also be run continuously for any suitable period of time, with reduced wear on the element 30 with the orifice therein, and on the blade 60. Suitable times include, but are not limited to greater than or equal to about: 30 minutes, 45 minutes, 1 hour, and any increment of 30 minutes above 1 hour.

EXAMPLE 1

The following describes one non-limiting example of a process for using a SONOLATOR® with at least one of the components described herein. In this example, the process may be used to produce a stable composition comprising an inorganic aggregate. Such a composition may, for example, comprise an improved version of a bismuth-containing liquid pharmaceutical composition. Bismuth-containing liquid pharmaceutical compositions are described in U.S. Pat. No. 4,940,695 issued to Coveney, et al. and U.S. Pat. No. 5,013,560 issued to Stentz, et al. A well-known example of such a composition is PEPTO-BISMOL® sold by The Procter & Gamble Company. This process and the compositions formed also comprise inventions in their own right.

Such a bismuth-containing liquid pharmaceutical composition may comprise several components. These include: a bismuth-containing pharmaceutical agent; a suspension system capable of suspending the bismuth-containing pharmaceutical agent and other components in an aqueous media; water; preservatives such as benzoic acid and sorbic acid; and optional ingredients.

The bismuth-containing pharmaceutical agent may be in the form of a phamaceutically-acceptable salt. Suitable bismuth-containing pharmaceutical agents include, for example, bismuth aluminate, bismuth subcarbonate, bismuth subcitrate, bismuth citrate, tripotassium dicitrato bismuthate, bismuth galate, bismuth subgalate, bismuth subnitrate, bismuth tartrate, bismuth subsalicylate, and mixtures thereof. Bismuth citrate and bismuth galate are soluble in water, and do not need to be deaggregated. Such pharmaceutical compositions typically comprise, by weight, from about 0.1% to about 5%, alternatively from about from about 0.5% to about 5%, from about 1% to about 4%, or from about 1.6% to about 1.9% of a bismuth-containing pharmaceutical agent.

The suspension systems may comprise a pharmaceutically-acceptable non-ionic cellulose ether polymer, magnesium aluminum silicate, or mixtures thereof. Suitable cellulosic suspending agents such as non-ionic cellulose ether polymers are selected from the group consisting of alkylcelluloses (e.g., methylcellulose), hydroxyalkylalkylcelluloses (e.g., hydroxypropylmethylcellulose: hydroxybutylmethylcellulose; hydroxyethylmethylcellulose; ethylhydroxyethylcellulose), hydroxyalkylcelluloses (e.g., hydroxyethylcellulose; hydroxypropylcellulose), and mixtures thereof. Representative examples of pharmaceutically-acceptable non-ionic cellulose ether polymers are: METHOCEL A® (methylcellulose, sold by The Dow Chemical Company); METOLOSE SM® (methylcellulose, sold by Shin Etsu Chemical Products, Ltd.); and METHOCEL E® (hydroxypropylmethylcellulose, sold by The Dow Chemical Company). The pharmaceutical compositions typically comprise, by weight, from about 0.1% to about 5%, alternatively from about 0.1% to about 3%, from about 0.5% to about 1.5%, or from about 0.8% to about 1.2%, of a non-ionic cellulose ethyl polymer.

The suspension system of the compositions described herein may also be clay-based and comprise a magnesium aluminum silicate, kaolin, and combinations thereof. Magnesium aluminum silicate (or aluminum magnesium silicate) has the formula $Al_2MgO_8Si_2$, and occurs naturally in such smectite minerals as colerainite, saponite, and sapphirine. Refined magnesium aluminum silicates useful herein are readily available, such as VEEGUM® magnesium aluminum silicate manufactured by R. T. Vanderbilt Company, Inc. The pharmaceutical compositions typically comprise, by weight, from about 0.1% to about 5%, alternatively from about 0.1% to about 3%, from about 0.5% to about 1.5%, or from about 0.8% to about 1.2%, of a magnesium aluminum silicate.

Another potentially useful material for suspension systems is xanthan gum, or a mixture of xanthan gum and magnesium aluminum silicate. Xanthan gum is a high molecular weight polysaccharide produced through pure culture fermentation of carbohydrates by the microorganism *Xanthomonas camoestris*. Xanthan gum is available from a variety of commercial sources, including RHODIGEL (sold by Rhone Poulenc Industries) and KELTROL (sold by Kelco Division of Merck & Co., Inc.). Xanthan gum is typically used at a level of from about 0.1% to about 5%, alternatively from about 0.1% to about 3%, or from about 0.5% to about 1.5%.

The suspension systems for the compositions described herein typically comprise from about 0.1% to about 10%, alternatively from about 0.5% to about 5%, or from about 1% to about 3%, by weight of the composition.

The liquid compositions described herein further comprise from about 80% to about 99%, alternatively from about 90% to about 99%, or from about 93% to about 98% water.

The compositions may comprise preservatives such as benzoic acid and sorbic acid. The composition may comprise from about 0.01% to about 0.075%, alternatively from about 0.01% to about 0.06%, or from about 0.025% to about 0.05%, of benzoic acid. The composition may comprise from about 0.01% to about 0.04%, alternatively from about 0.01% to about 0.03%, or from about 0.0125% to about 0.025%, of sorbic acid. The weight percent ranges of these preservative components are by weight of the protonated species, whether or not all of the acids are in the protonated form in the composition.

The pharmaceutical compositions may comprise additional optional components selected as appropriate for the particular composition being prepared. The choice of pharmaceutically-acceptable optional components to be used in the compositions is basically determined by the properties, especially aesthetic properties, desired for the composition.

Some examples of substances which can serve as pharmaceutically-acceptable optional components are sugars such as lactose, glucose and sucrose; non-nutritive sweeteners such as saccharin, aspartame, acesulfame, and cyclamate; coloring agents; flavoring agents such as methyl salicylate; etc. A preferred optional component is salicylic acid which may be used to reduce pH and/or provide some preservative benefit. Other compatible pharmaceutical additives and actives (e.g., NSAI drugs; $H_2$ receptor blocking anti-secretory agents) may be included in the pharmaceutically-acceptable optional components for use in these compositions.

The following examples further describe and demonstrate embodiments within the scope of the present invention. These examples are given solely for the purpose of illustration, and are not to be construed as a limitation of the present invention since many variations thereof are possible without departing from its spirit and scope.

PEPTO BISMOL® liquid can be made by preparing separate intermediates of magnesium aluminum silicate (such as VEEGUM®), methylcellulose ("methocel"), and bismuth subsalicylate ("BSS") in water. These intermediates can be sent separately through the SONOLATOR® where the desired transformations, such as dispersion, hydration and de-aggregation are performed on them. The processes of interest herein may include fewer than all of these transformations, and may, but need not, include all of the steps described below. The intermediates can be formed in any order. In addition, any one or more of the steps described below may be combined.

One of the problems encountered in attempting to prepare PEPTO BISMOL® liquids in a SONOLATOR® is the erosion of stainless steel parts (blade and orifice) typically supplied with the SONOLATOR® caused by the impact of bismuth subsalicylate crystalline panicles on these surfaces. In the process described below, a Model "A" SONOLATOR® high pressure homogenizer is used with a synthetic diamond blade.

VEEGUM® Addition

1.) A quantity of ambient temperature (20-30° C.) water equal to 20% by weight of the final batch weight is added to a tank equipped with an agitator.

2.) The total formula quantity of VEEGUM® (obtained from R.T. Vanderbilt Company, Norwalk, Conn., U.S.A.) is charged to the funnel of a TRIBLENDER™ mixer. The TRIBLENDER™ mixer is obtained from Tri Clover, a division of Alfa Laval, Lund, Sweden. The TRIBLENDER™ mixer incorporates solids into a high velocity stream of water by means of the Venturi effect. When a vacuum is established, the solids are sucked or drawn into the water.

3.) The stream of VEEGUM® in water is then pumped to the SONOLATOR® at 60-90 psi (0.41-0.62 MPa). This head pressure is used to allow the SONOLATOR® pump to draw the VEEGUM®/water mixture into the orifice of the SONOLATOR®.

4.) The VEEGUM®/water mixture is forced through the SONOLATOR® orifice at high pressure. The VEEGUM®/water mixture is at a pressure of 600-2,000 psi. (4.1-14 MPa) as it enters the orifice of the SONOLATOR®.

5.) The VEEGUM®/water mixture is directed at the blade inside the SONOLATOR®. The blade is optimally set between 2.5 to 5.25 turns from the farthest possible position away from the orifice. (The 2.5 turn position is about halfway between the farthest position away from the orifice and the closest position adjacent to the orifice. The 5.25 turn position is directly adjacent to the orifice. The same setting is used for the other transformations in this example.)

6.) As the VEEGUM®/water mixture exits the SONOLATOR® orifice, it expands and impacts against the blade. During this expansion, the pressure drops and cavitation occurs in regions near the blade, which ultrasonically resonates. Without wishing to be bound by any particular theory, cavitation is believed to be the mechanism of energy transfer to the mixture. The bubbles that are formed implode and produce pressure waves that generate the energy that causes the desired transformations. For VEEGUM®, the desired transformation is the separation of VEEGUM® plates from their stacked arrangement into individual plates (dispersion), which are then more susceptible to hydration in water.

7.) The dispersed, hydrated VEEGUM®/water mixture leaves the SONOLATOR® through holes at the back of the SONOLATOR®. The size of these holes is controlled by means of a back pressure setting dial on the SONOLATOR®. As the back pressure is increased, the holes close, and the VEEGUM®/water mixture is retained in the SONOLATOR® for longer periods of time. The pressure differential from upstream of the orifice to downstream of the orifice decreases and cavitation is reduced. For all the transformations in this example, the back pressure setting is zero to 2 turns inward (fully open to slightly closed).

8.) The VEEGUM®/water mixture is then pumped to the final batch tank where it is collected without agitation.

9.) A quantity (7-10% of the final batch weight) of chilled (5-12° C.) water is added to the VEEGUM®/water mixture in the batch tank.

Methylcellulose Addition

10.) A quantity of hot (45-70° C.) water equal to 20% by weight of the final batch weight is added to a tank equipped with an agitator.

11.) The total formula quantity of methylcellulose (available from Dow Chemical Company, Midland, Mich., U.S.A.) is charged to the funnel of a TRIBLENDER™ mixer. When a vacuum is established, the methylcellulose is drawn into the water.

12.) The stream of methylcellulose in water is pumped at 6090 psi (0.41-0.62 MPa) to the SONOLATOR®.

13.) The methylcellulose/water mixture is forced through the SONOLATOR® orifice at high pressure. The methylcellulose/water mixture is at a pressure of 400-1,500 psi (2.8-10 MPa) as it enters the orifice of the SONOLATOR®.

14.) The methylcellulose/water is directed at the blade inside the SONOLATOR. As the methylcellulose/water mixture exits the orifice, it expands and impacts against the blade. As before, cavitation occurs in regions near the blade, and the desired transformation occurs. For methylcellulose, this transformation is the separation of methylcellulose polymer chains from their intertwined/hydrogen-bonded arrangement to individual strands (dispersion), which are then more susceptible to hydration in cold water.

15.) The dispersed methylcellulose/water mixture leaves the SONOLATOR® through holes at the back of the SONOLATOR®.

16.) The methylcellulose/water mixture is then pumped to the final batch tank where it is added to the chilled VEEGUM®/water mixture with agitation.

17.) A quantity (7-10% of the batch weight) of chilled (5-12° C.) water is added to the VEEGUM®/methylcellulose/water mixture. The temperature of this mixture is set below 30° C. in order to proceed to the next step.

18.) A dye solution pre-mix is added and mixed at this step.

Bismuth Subsalicylate Dry Powder Addition

19.) A quantity of ambient temperature (20-30° C.) water equal to 20% by weight of the final batch weight is added to a tank equipped with an agitator.

20.) The total formula quantity of BSS (available from MCP Metal Specialties, Inc., Fairfield, Conn., U.S.A.) is charged to the funnel of a TRIBLENDER™ mixer. When a vacuum is established, the BSS is sucked into the water.

21.) The stream of BSS in water is then pumped at 60-90 psi (0.41-0.62 MPa) to the SONOLATOR®.

22.) The BSS/water mixture is at a pressure of 300-1,200 psi (2-8.3 MPa) as it enters the orifice of the SONOLATOR®. The orifice made of stainless steel is susceptible to rapid erosion due to the impact of BSS particles. This erosion leads to an increase in the size of the orifice, which results in reduced operating pressures and decreased ability to affect the desired transformation. The use of a diamond or other materials of high hardness is believed to reduce the effect of orifice erosion due to particle impact.

23.) The BSS/water mixture is forced through the orifice at high pressure and impacts the blade. Stainless steel blades are subject to rapid erosion due to the impact of particles of BSS at high pressure. The use of a diamond blade resists erosion due to BSS particle impact.

24.) As the stream of BSS/water exits the orifice, it expands and impacts against the blade. As before, cavitation occurs in regions near the blade, and the desired transformation occurs. For BSS, this transformation is the de-aggregation of crystals which disrupts BSS aggregates into easy-to-suspend single crystals.

25.) The transformed (de-aggregated) BSS leaves the SONOLATOR® through holes at the back of the SONOLATOR®.

26.) The BSS/water mixture is then pumped to the final batch tank where it is added to chilled VEEGUM®/methylcellulose/water mixture with agitation.

27.) A pre-mix, containing flavors, buffers and preservatives is added at this point with agitation.

28.) The batch is then completed by adding ambient temperature water with agitation in the quantity required to give the final batch weight.

Such a process may provide a number of benefits. It should be understood, however, that obtaining such benefits is not required unless specified in the appended claims. One benefit is the ability to provide a narrower particle size distribution and a smaller average particle size of the bismuth-containing pharmaceutical agent in a single pass through the SONOLATOR® than is possible unless using many passes through other types of mixing devices such as high shear mixers. Smaller sized particles are useful in providing a more stable composition, which is less susceptible to having the ingredients settle out. Smaller sized particles of the bismuth-containing pharmaceutical agent also allow reduced quantities of suspending agents to be used. For example, the amount of the ingredients marked with the asterisk in the table below may be about 10% lower than that required in prior processes which use high shear mixers. Another benefit is that the transformations may be more efficient in that they may progress further toward their completion than when other types of mixing devices are used. In addition, the components described herein may be sufficiently durable to allow the apparatuses to be used to make large scale quantities of the compositions of interest. The process described herein may also be capable of being carried out over a shorter time period (e.g., in approximately half the time) as processes which use other types of mixing devices, making it a more efficient and economical process.

Non-limiting examples of bismuth-containing compositions that can be made with the process described herein are set out below.

EXAMPLES 2-5

Bismuth-Containing Compositions

| Ingredient | % weight percent | | | |
| --- | --- | --- | --- | --- |
| | Ex. 2 | Ex. 3 | Ex. 4 | Ex. 5 |
| Bismuth Subsalicylate | 1.7700 | 3.5400 | 1.7700 | 3.5400 |
| Methylcellulose | 0.9774* | 0.9774* | 0.8000 | 0.8000 |
| Magnesium Aluminum Silicate | 0.8932* | 0.8932* | 0.8000 | 0.8000 |
| Methyl Salicylate | 0.0888 | 0.0888 | 0.0888 | 0.0888 |
| Salicylic Acid | 0.0710 | 0.0710 | 0.0710 | 0.0710 |
| Sodium Saccharin | 0.0612 | 0.0612 | 0.0612 | 0.0612 |
| Sodium Salicylate | 0.0604 | 0.0604 | 0.0604 | 0.0604 |
| Benzoic Acid | 0.0250 | 0.0250 | 0.0250 | 0.0250 |
| Sorbic Acid | 0.0126 | 0.0126 | 0.0126 | 0.0126 |
| D&C Red # 22 | 0.0074 | 0.0074 | 0.0074 | 0.0074 |
| D&C Red # 28 | 0.0050 | 0.0050 | 0.0050 | 0.0050 |
| Purified Water (United States Pharmacopoeia (USP)) | 96.0280 | 94.2580 | 96.2986 | 94.2586 |

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm".

It should be understood that every maximum numerical limitation given throughout this specification includes every lower numerical limitation, as if such lower numerical limitations were expressly written herein. Every minimum numerical limitation given throughout this specification will include every higher numerical limitation, as if such higher numerical limitations were expressly written herein. Every numerical range given throughout this specification will include every narrower numerical range that falls within such broader numerical range, as if such narrower numerical ranges were all expressly written herein.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

The invention claimed is:

1. An apparatus for mixing by producing shear and/or cavitation, said apparatus comprising:
   a mixing chamber, said mixing chamber comprising an entrance, at least one inlet, and an outlet;
   an element with an orifice therein, said element being located adjacent the entrance of said mixing chamber, wherein said element comprises portions surrounding said orifice, and at least some of said portions surrounding said orifice have a hardness of greater than that of cemented tungsten carbide; and
   a blade for use in said apparatus for mixing by producing shear and/or cavitation, said blade having a tapered leading edge, wherein the leading edge of said blade is provided with a Vickers hardness of greater than or equal to about 20 GPa;
   wherein the apparatus can be operated continuously for greater than about 30 minutes at a pressure greater than about 1,000 psi.

2. The apparatus of claim 1 wherein said at least some of said portions surrounding said orifice have a Vickers hardness of greater than or equal to about 20 GPa.

3. The apparatus of claim 1 wherein said at least some of said portions surrounding said orifice have a Vickers hardness that is between about 20 and about 100 GPa.

4. The apparatus of claim 1 wherein said at least some of said portions surrounding said orifice have a Vickers hardness that is between about 30 and about 95 GPa.

5. The apparatus of claim 1 wherein said at least some of said portions surrounding said orifice have a Vickers hardness that is between about 60 and about 95 GPa.

6. The apparatus of claim 1 wherein said at least some of said portions surrounding said orifice are at least partially comprised of one or more of the following materials: silicon nitride, titanium nitride, aluminum oxide, silicon carbide, titanium carbide, boron carbide, titanium diboride, boron oxide, rhenium diboride, cubic boron nitride, cubic $BC_2N$, diamond-like carbon, diamond, composites of diamond and cubic boron nitride, and coatings of any of these materials, including diamond-coated materials and diamond-like carbon.

7. The apparatus of claim 6 wherein said at least some of said portions surrounding said orifice comprise a diamond coating.

8. The apparatus of claim 6 wherein said at least some of said portions surrounding said orifice comprise a bulk diamond structure.

9. The apparatus of claim 1 wherein said blade is in said mixing chamber disposed opposite the element with an orifice therein.

10. The apparatus of claim 9 wherein the leading edge of said blade has a Vickers hardness that is between about 20 and about 100 GPa.

11. The apparatus of claim 9 wherein the leading edge of said blade has a Vickers hardness that is between about 30 and about 95 GPa.

12. The apparatus of claim 9 wherein the leading edge of said blade has a Vickers hardness that is between about 60 and about 95 GPa.

13. The apparatus of claim 9 wherein said blade comprises at least one material having a predicted acoustic velocity greater than or equal to about 7,640 m/s.

14. The apparatus of claim 9 wherein said blade undergoes harmonic vibration at a frequency of from about 15 kHz to 100 kHz.

15. The apparatus of claim 9 wherein said blade undergoes harmonic ultrasonic vibration at a frequency of from about 20 to about 40 kHz.

16. The apparatus of claim 1 wherein said leading edge of said blade is comprised of one or more of the following materials: silicon nitride, titanium nitride, aluminum oxide, silicon carbide, titanium carbide, boron carbide, titanium diboride, boron, oxide, rhenium diboride, cubic boron nitride, cubic $BC_2N$, diamond-like carbon, diamond, composites of diamond and cubic boron nitride, and coatings of any of these materials, including diamond-coated materials and diamond-like carbon.

17. The apparatus of claim 16 wherein said leading edge of said blade comprises a diamond coating.

18. The apparatus of claim 16 wherein at least said leading edge of said blade comprises a bulk diamond structure.

19. The apparatus of claim 16 wherein said entire blade comprises a bulk diamond structure.

20. The apparatus of claim 9 wherein said blade comprises a material having an elastic modulus of greater than or equal to about 700 GPa.

21. The apparatus of claim 9 wherein said blade comprises at least one material having a density of less than or equal to about 12 g/cm$^3$.

22. The apparatus of claim 1 wherein said orifice is slot-shaped.

23. The apparatus of claim 1 wherein said blade comprises a material having an elastic modulus of greater than or equal to about 700 GPa.

24. The apparatus of claim 1 wherein said blade comprises at least one material having a density of less than or equal to about 12 g/cm$^3$.

25. The apparatus of claim 1 wherein said blade comprises at least one material having a predicted acoustic velocity greater than or equal to about 7,640 m/s.

26. The apparatus of claim 1 wherein said blade undergoes harmonic vibration at a frequency of from about 15 kHz to 100 kHz.

27. The apparatus of claim 1 wherein said blade comprises a material that undergoes harmonic ultrasonic vibration at a frequency of from about 20 to about 40 kHz.

* * * * *